US00PP33868P2

(12) United States Plant Patent
NeSmith

(10) Patent No.: US PP33,868 P2
(45) Date of Patent: Jan. 18, 2022

(54) SOUTHERN HIGHBUSH BLUEBERRY PLANT NAMED 'TH-920'

(50) Latin Name: *Vaccinium corymbosum*
Varietal Denomination: TH-920

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/229,488

(22) Filed: Apr. 13, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Thomas Horstemeyer, LLP

(57) ABSTRACT

A new and distinct cultivar of *Vaccinium* plant named 'TH-920', characterized by a combination of early-to-mid season ripening; large berries with good scar and flavor and high fruit quality; moderately vigorous growth suited to home gardens, soft pink flowers at opening, bronze coloring to newly emerging foliage, berries transitioning from pink hued to sky-blue during ripening; and a chilling requirement of about 500-550 hours below about 45° F.

6 Drawing Sheets

Botanical designation: *Vaccinium corymbosum.*
Cultivar denomination: 'TH-920'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-920'.

The new *Vaccinium corymbosum* 'TH-920' was first identified in 2005 in Griffin, Ga. The new variety 'TH-920' is early-to-mid season, ripening earlier than some early commercial varies in south and middle Georgia and has moderately vigorous growth and compact form making it well-suited for home gardens. 'TH-920' has large berries with good scar, good flavor, overall high quality fruit, and a chilling requirement of about 500-550 hours below about 45° F. The new variety 'TH-920' also has aesthetic appeal as a home garden plant with beautiful soft-pink hued flowers, bronze colored emerging foliage, and berries with a pink hue before ripening that turns sky-blue in ripe fruit.

'TH-920' is a product of a cross of 'TH-647' X 'Windsor' made by D. Scott NeSmith in 2002. 'TH-647' is a non-patented breeding line, and 'Windsor' is a patented variety (U.S. Plant Pat. No. 12,783). The new blueberry plant variety 'TH-920' has been tested in asexually propagated (by vegetative cuttings) plantings in Alapaha, Ga. since 2007 where it was established for testing and comparing to industry standards. 'TH-920' was also observed in a trial in Griffin, Ga. from 2007 through 2014. Observations of the resulting 'TH-920' progeny have shown that the unique features of this new *Vaccinium corymbosum* 'TH-920' are stable and reproduced true to type in successive generations.

SUMMARY OF THE INVENTION

The new *Vaccinium* cultivar 'TH-920' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-920'. In combination, these traits set 'TH-920' apart from all other existing varieties of southern highbush blueberry known to the inventors:

1. early-to-mid season, ripening later than early commercial variety 'Rebel' but before later commercial variety 'Camellia' in south and middle Georgia;
2. large fruit with good scar and flavor and overall high quality as compared to 'Rebel' and 'Camellia';
3. moderately vigorous growth with compact form well-suited to home gardens;
4. chilling requirement of about 500-550 hours below about 45° F. (based on comparison of flowering dates with those of known standard cultivars);
5. soft pink flowers at opening, bronze cast to newly emerging foliage, and berries with pink hue transitioning to sky-blue during ripening.

Comparison: As compared to the female parent 'TH-647' and male parent 'Windsor', plants of the new *Vaccinium* cultivar 'TH-920' have a chilling requirement of about 500-550 hours, which is similar to 'TH-647' (500 to 600 hours) but higher than 'Windsor' (250 to 350 hours). 'TH-920' flowers and ripens similar to the time of 'TH-647' but 5 to 8 days later than 'Windsor'. Berry size of 'TH-920' is similar to 'Windsor' (2.2 to 2.5 g/berry) but much larger than 'TH-647' (1.8 to 2.0 g/berry). 'TH-920' has a good to very good picking scar (similar to 'TH-647') that typically remains dry after harvest; whereas 'Windsor' picking scar can be wet. 'TH-920' firmness is similar to 'Windsor', but less than 'TH-647'.

Plants of the new *Vaccinium corymbosum* can also be compared to to early season southern highbush blueberry cultivar 'Rebel' (U.S. Plant Pat. No. 18,138) and later variety 'Camellia' (U.S. Plant Pat. No. 18,151). The selection 'TH-920' begins flowering and ripening later than early variety 'Rebel' but before later variety 'Camellia' in south and middle Georgia. 'TH-920' has large berries with good scar, and good flavor, as compared to 'Camellia' and 'Rebel' at Alapaha and Griffin, Ga. over a 5-year period (Tables 1 and 2), and overall high quality fruit as compared to 'Camellia' and 'Rebel' in Griffin, Ga. from 2010-2013 (Table 3). Plants are moderately vigorous, but compact, making them well suited for home gardeners. No notable diseases or other pest problems have been observed for the new variety that are not also common for other varieties. The new variety is estimated to have a chilling requirement of about 500-500 hours, more or less, below about 45° F. (based on comparison of flowering dates with those of known standard cultivars) when produced under typical low to mid chill production regions. Additional comparison data of 'TH-920' with 'Camellia' and 'Rebel' are presented in the tables below.

The new *Vaccinium* 'TH-920' has considerable aesthetic appeal as a home garden plant too, producing flowers having a beautiful soft pink hue as they begin to open (FIGS. 1A and 1B). Newly emerging foliage has a notable bronze coloring (FIG. 2B). The plant is also attractive during fruiting with berries displaying a pink hue as they size prior to ripening (FIGS. 2A-2B and FIG. 4A) and developing a sky-blue color in ripe fruit providing a pleasing contrast with lush green foliage as berries ripen (FIG. 3 and FIG. 4B).

TABLE 1

5-year average ratings of some fruit and plant characteristics of homeowner blueberry 'TH-920' and commercial cultivars Camellia and Rebel (2009-2013) in field test plots at Alapaha, Ga. Rating scales are based on a 1 to 10 score, with 1 being the least desirable and 10 being the most desirable. Plants were established in 2007.

| | Alapaha location | | |
|---|---|---|---|
| Attribute | 'Rebel' | 'Camellia' | 'TH-920' |
| Berry size | 7.7 ± 0.2 | 8.9 ± 0.2 | 8.9 ± 0.2 |
| Berry scar | 7.4 ± 0.2 | 7.2 ± 0.2 | 7.5 ± 0.2 |
| Berry color | 7.2 ± 0.2 | 8.7 ± 0.2 | 8.8 ± 0.2 |
| Berry firmness | 7.8 ± 0.1 | 7.2 ± 0.1 | 7.0 ± 0.1 |
| Berry flavor | 6.7 ± 0.1 | 7.8 ± 0.1 | 7.7 ± 0.1 |
| Cropping | 4.9 ± 1.6 | 5.4 ± 0.3 | 5.2 ± 0.5 |
| Plant vigor | 8.4 ± 0.4 | 9.8 ± 0.2 | 8.3 ± 0.2 |
| Date of 50% flowering | Feb. 24 | Mar. 11 | Mar. 15 |
| Date of 50% ripening | May 3 | May 15 | May 8 |
| Fruit development period (days) | 67.3 ± 4.5 | 65.3 ± 4.9 | 51.3 ± 0.7 |

TABLE 2

5-year average ratings of some fruit and plant characteristics of homeowner blueberry 'TH-920' and commercial cultivars Camellia and Rebel (2009-2013) in field test plots at Griffin, Ga. Rating scales are based on a 1 to 10 score, with 1 being the least desirable and 10 being the most desirable. Plants were established in 2007.

| | Griffin location | | |
|---|---|---|---|
| Attribute | 'Rebel' | 'Camellia' | 'TH-920' |
| Berry size | 7.5 ± 0.1 | 8.6 ± 0.2 | 8.5 ± 0.1 |
| Berry scar | 7.5 ± 0.1 | 7.0 ± 0.1 | 7.3 ± 0.1 |
| Berry color | 7.2 ± 0.1 | 7.9 ± 0.2 | 8.8 ± 0.1 |

TABLE 2-continued 5-year average ratings of some fruit and plant characteristics of homeowner blueberry 'TH-920' and commercial cultivars Camellia and Rebel (2009-2013) in field test plots at Griffin, Ga. Rating scales are based on a 1 to 10 score, with 1 being the least desirable and 10 being the most desirable. Plants were established in 2007.

| | Griffin location | | |
|---|---|---|---|
| Attribute | 'Rebel' | 'Camellia' | 'TH-920' |
| Berry firmness | 7.4 ± 0.1 | 7.2 ± 0.1 | 6.8 ± 0.1 |
| Berry flavor | 6.6 ± 0.2 | 7.4 ± 0.2 | 7.7 ± 0.1 |
| Cropping | 4.9 ± 1.1 | 7.9 ± 0.2 | 6.5 ± 0.5 |
| Plant vigor | 6.3 ± 0.3 | 9.8 ± 0.1 | 7.9 ± 0.3 |
| Date of 50% flowering | Mar. 8 | Mar. 25 | Mar. 23 |
| Date of 50% ripening | May 12 | May 31 | May 25 |
| Fruit development period (days) | 65.2 ± 7.5 | 67.3 ± 4.8 | 59.3 ± 2.4 |

TABLE 3

Berry weight, firmness, and Brix for two commercial southern highbush blueberry cultivars, 'Rebel' and 'Camellia', and 'TH-920' grown in Griffin, GA during 2010-2013.

| Selection or cultivar | Berry weight (g/25 fruit) | Berry firmness (g/mm) | Berry Brix (%) |
|---|---|---|---|
| Camellia | 54.2 ± 9.3 | 168 ± 5.0 | 13.9 ± 0.4 |
| Rebel | 46.1 ± 9.9 | 180 ± 5.4 | 11.9 ± 0.5 |
| TH-920 | 51.6 ± 3.6 | 162 ± 1.4 | 12.6 ± 0.6 |

BRIEF DESCRIPTION OF THE DRAWINGS

The accompanying colored photographic illustrations show the overall appearance and distinct characteristics of the new cultivar of *Vaccinium corymbosum* 'TH-920' showing the colors as true as possible. Colors in the photographs may differ slightly from the color values cited in the detailed botanical description, which accurately describes the colors of the new *Vaccinium corymbosum* 'TH-920'. Photographs were taken of plants grown outdoors in Alapaha, Ga. and Griffin, Ga. during different years.

The photographs labeled

The photographs labeled

The photograph labeled

The photographs labeled FIG. 4A depicts maturing fruit on a branch of a typical 5-year old 'TH-920' plant showing berries in various stages of ripening with color from light pink (pre-ripened) to sky-blue (ripe). FIG. 4B depicts a close-up view of ripe fruit of 'TH-920' in a human hand, showing the sky-blue fruit color, taken in Griffin, Ga. May 2012.

DETAILED BOTANICAL DESCRIPTION

Figure 1A:
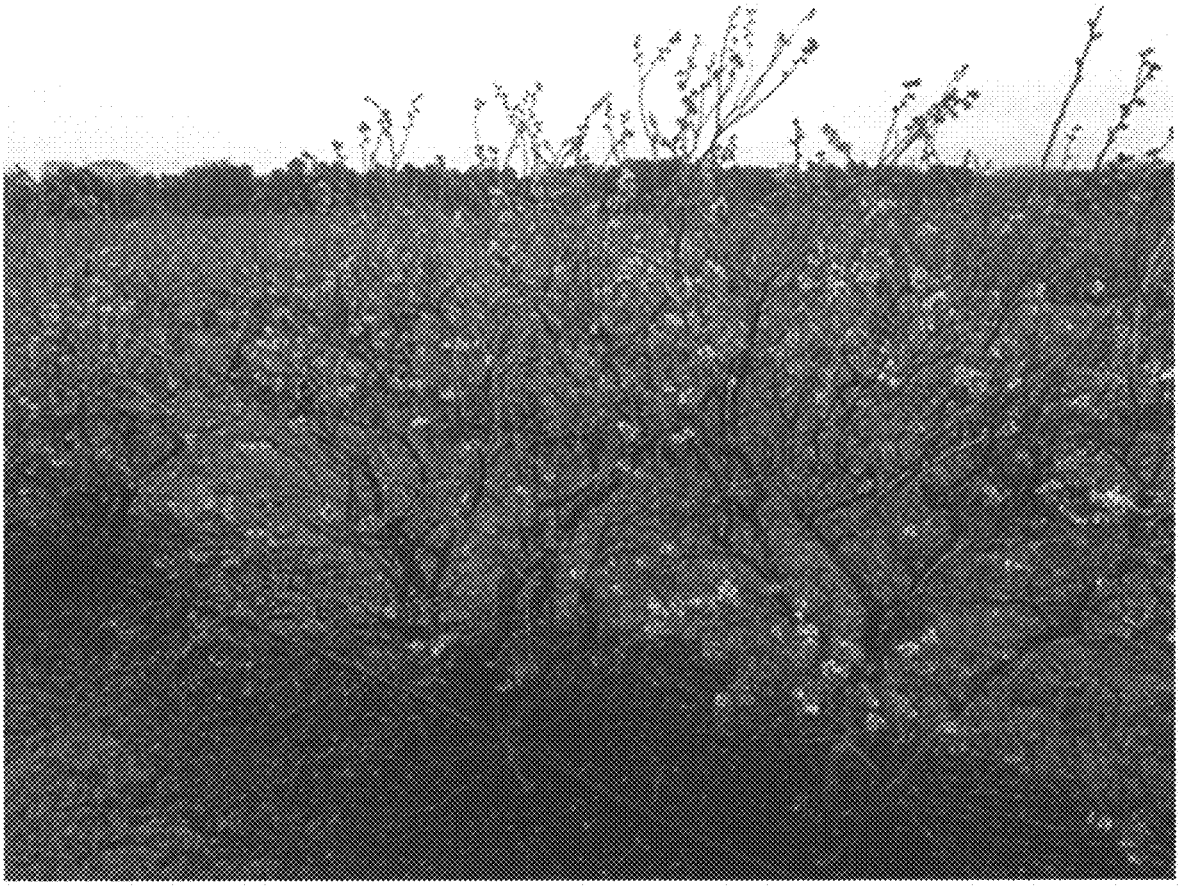
FIGS. 1A and 1B depict 5-year old plants of 'TH-920' showing pink flower color, with FIG. 1A showing a row of several 'TH-920' plants and FIG. 1B showing a closer view of branches of a 'TH-920' plant. Photographs were taken in March 2012 in Griffin, Ga.
Figure 1B:
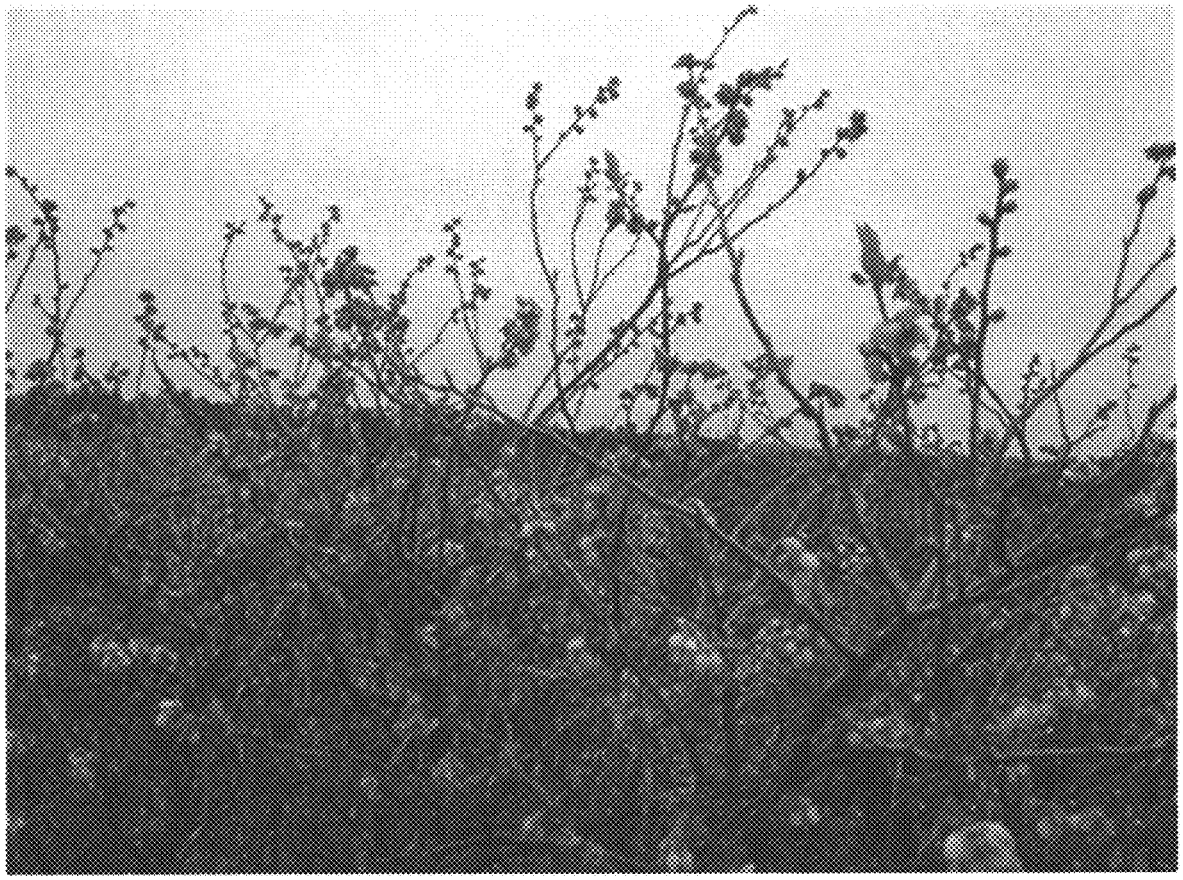
Figure 2A:
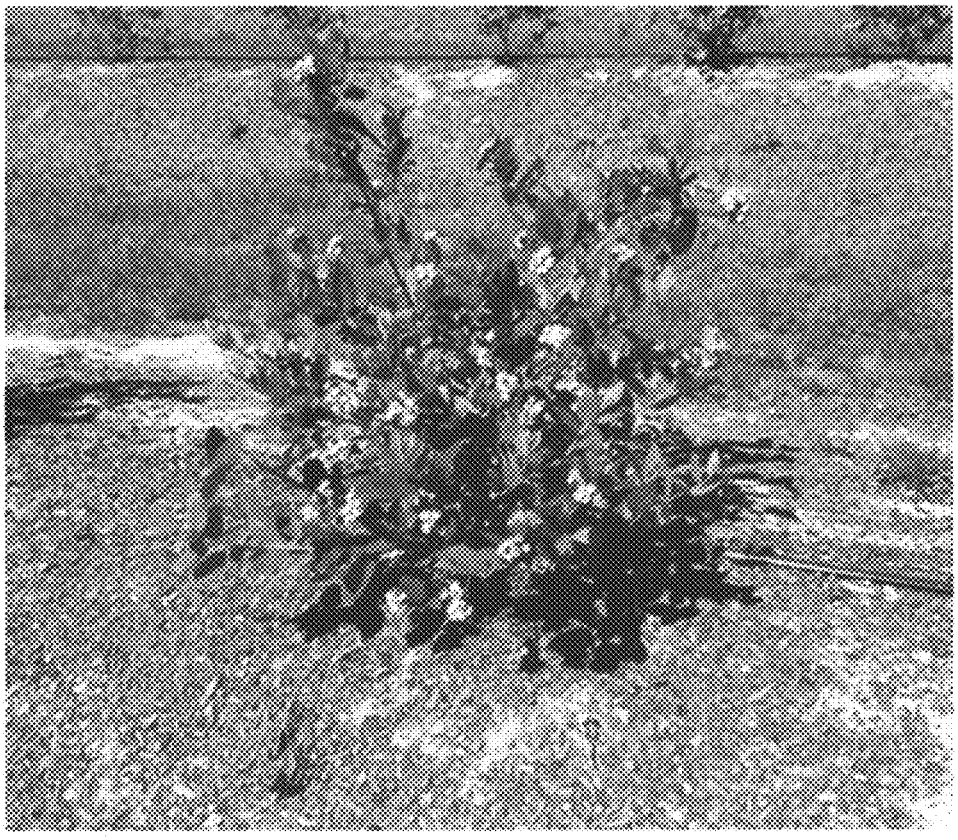
FIGS. 2A and 2B depict typical 2- and 4-year old 'TH-920' plants, respectively, displaying showy pre-ripened berries with a pink cast and bronze coloring in newly emerging foliage. Photographs were taken in Alapaha, Ga. in April 2012 and April 2014, respectively.
Figure 2B:
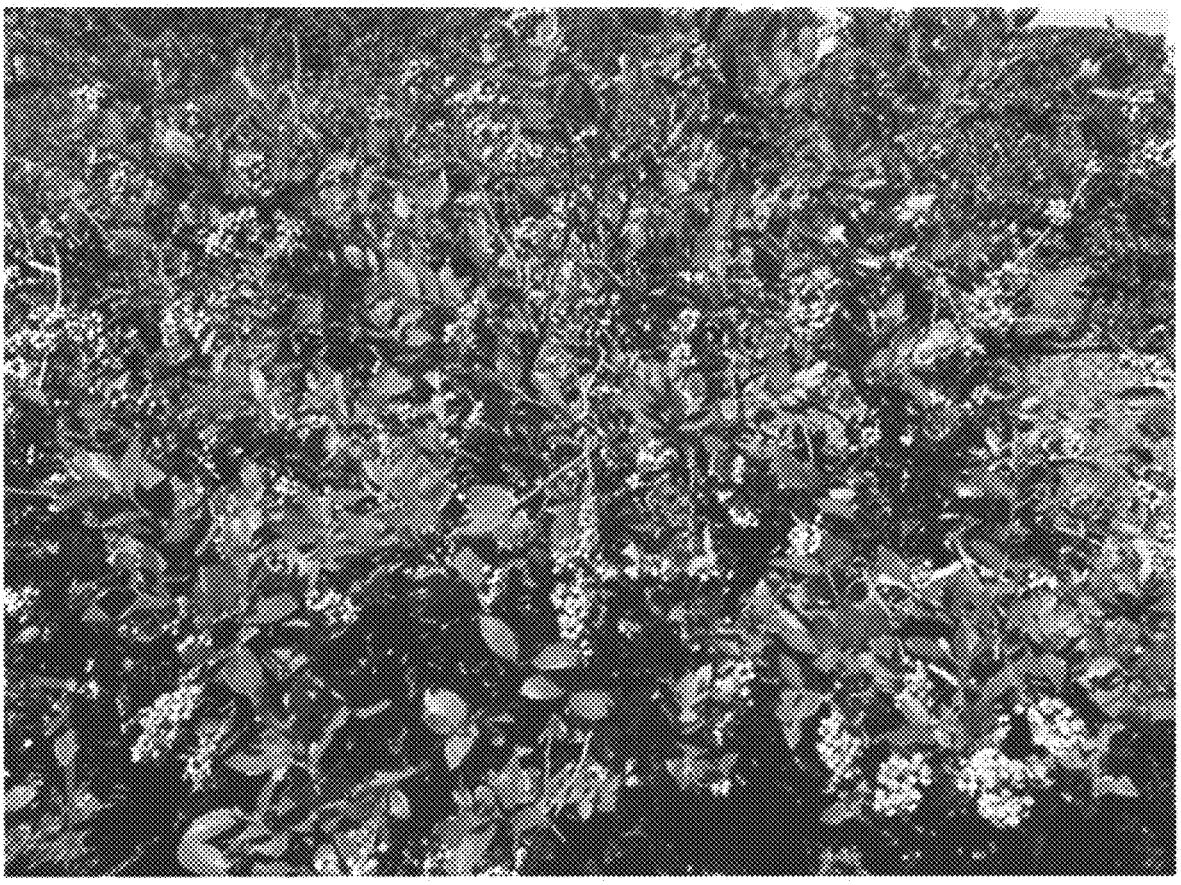
Figure 3:
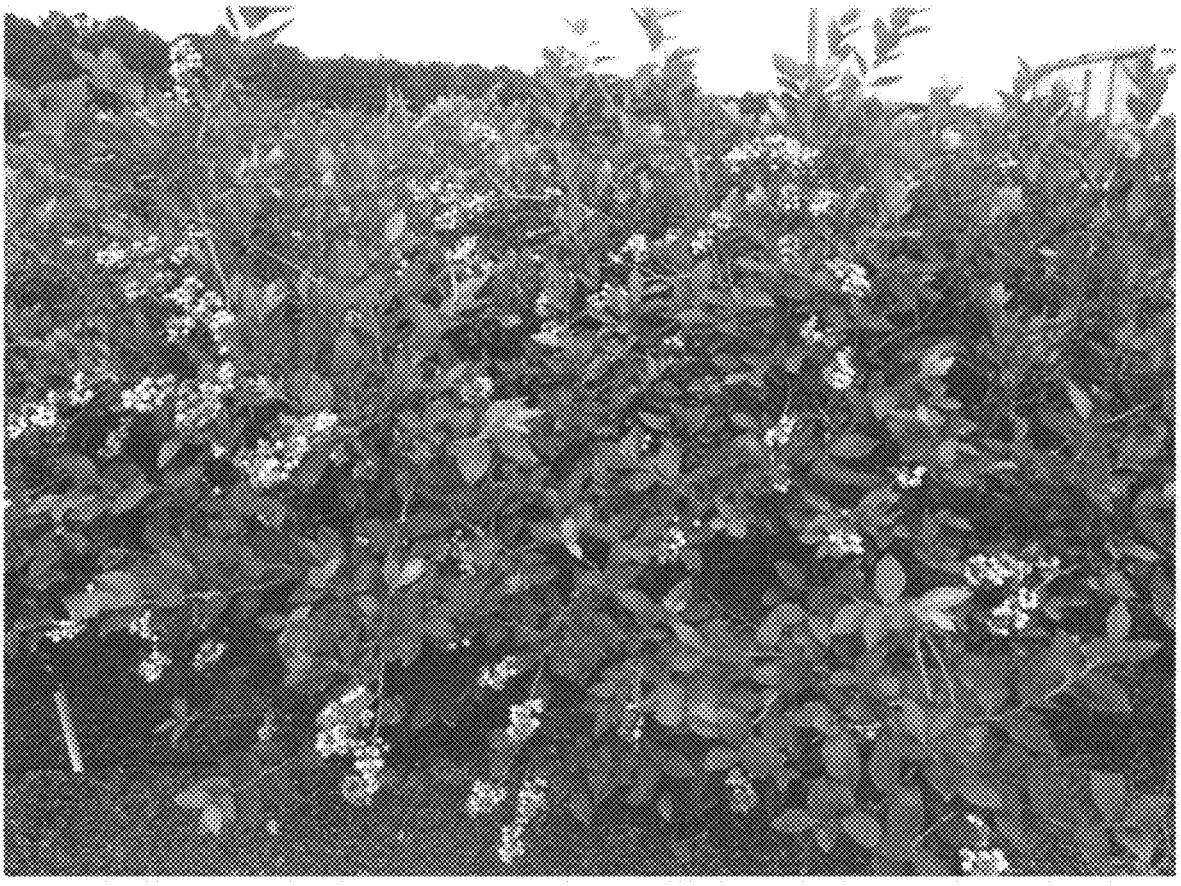
FIG. 3 depicts typical 5-year old 'TH-920' plants during fruit ripening in Griffin, Ga. taken in May 2012.
Figure 4A:
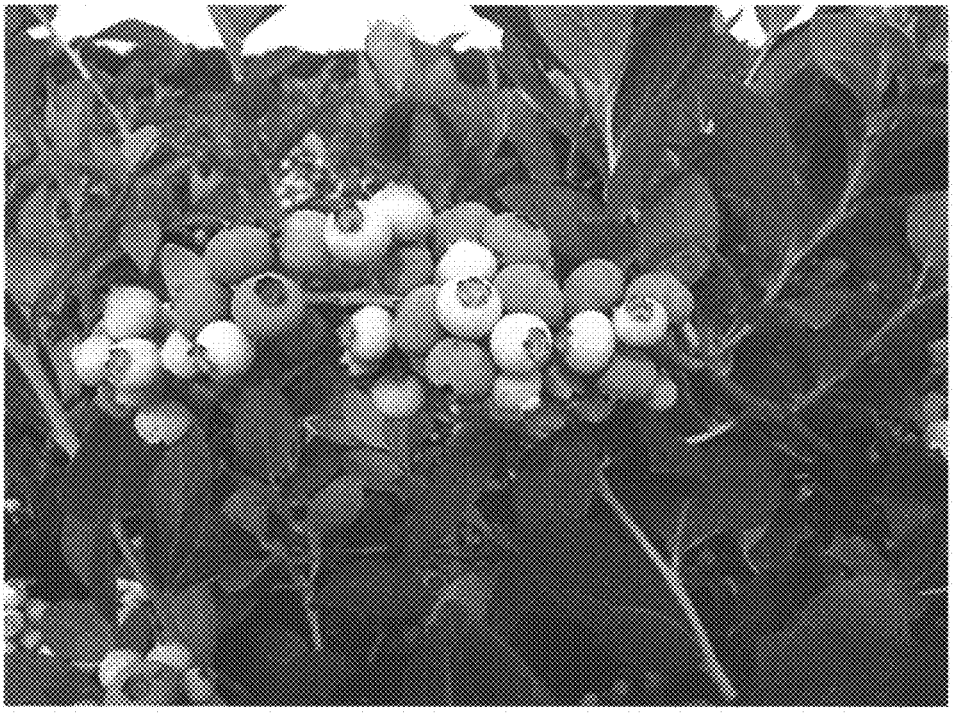
FIGS. 4A-4B depict close-up views of fruit of 'TH-920' plants.
Figure 4B:
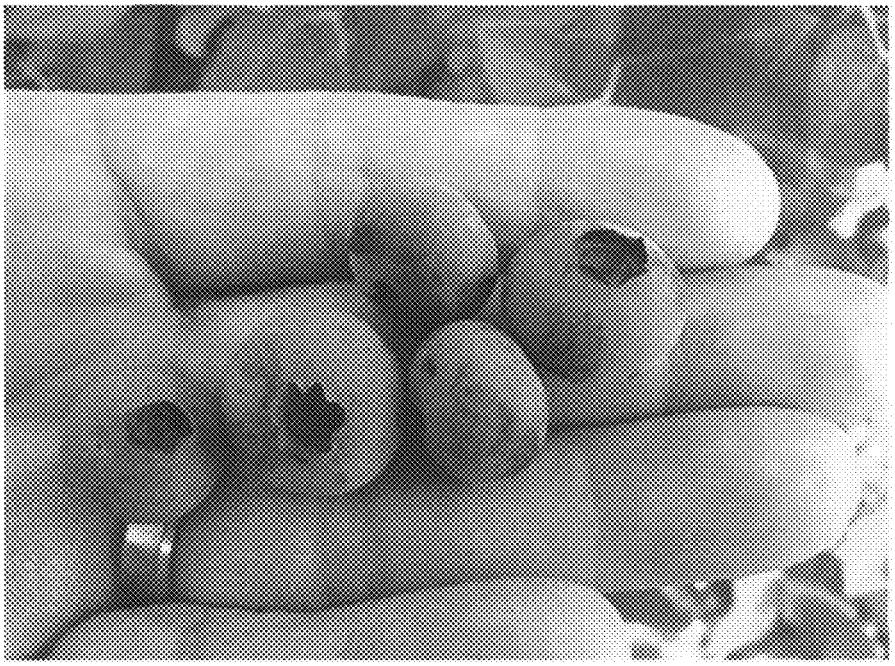

The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TH-920'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-920'. Where dimensions, sizes, colors, and other characteristics are given, it is to be understood that such characteristics are approximations and averages set forth as accurately as practicable. Data were collected between the years of 2009-2013 from horticulture farms and nurseries in Alapaha and/or Griffin, Ga. from 4 to 6-year-old plants (planted in the field with supplemental irrigation). The average low temperature for the year ranges from about 54° F. to 58° F., and the average high temperature for the year ranges from about 78° F. to 82° F.

Botanical classification: *Vaccinium corymbosum* 'TH-920'.

- *Commercial classification*.—Fruit-bearing shrub.
- *Parentage*.—'TH-647' (non-patented breeding line) and 'Windsor' (U.S. Plant Pat. No. 12,783).

Growth and propagation:

- *Propagation type*.—Vegetative by softwood cuttings.
- *Growth rate*.—Moderately vigorous.
- *Root description*.—Fibrous.

Plant description:

- *Growth habit*.—Plant is semi-spreading to spreading, with crown of about 10 to 15 cm diameter formed from fused canes about 10 cm or less above the soil surface. After about 10 cm, about 3 to 5 canes form.
- *Usage*.—Home gardens and limited commercial fruit production.
- *Productivity*.—High. Annual yields of about 8 to 12 lbs per plant each year on plants around 5 years old or older grown under well fertilized and irrigated field conditions.
- *Size of plant*.—Plant is about 1.5 to 1.7 m tall by about 4 years. The plant crown, or base, is narrow, typically about 10 to 15 cm in diameter. Upper portion of plant canopy reaches about 1.3 to 1.5 m in diameter by about 4 years.
- *Cold hardiness*.—Similar to southern highbush varieties such as 'Camellia' (U.S. Plant Pat. No. 18,151) and 'Star' (U.S. Plant Pat. No. 10,675).
- *Disease resistance*.—No exceptional disease resistance or susceptibility observed. Typical for southern highbush such as 'Camellia' and 'Star'.
- *Chilling requirement*.—Plants are medium chill, requiring only about 500 to 550 hours, more or less, of temperatures at or below about 7° C. to induce normal leafing and flowering. The chill requirement is more than the male parent 'Windsor' (U.S. Plant Pat. No. 12,783; 300 hours of chilling required), and slightly less than the female parent 'TH-647' (non-patented breeding selection; 550 to 600 hours of chilling required).
- *Leafing*.—Plants tend to break sufficient leaf buds simultaneously with, or shortly after, anthesis.
- *Canes*.—Main cane base diameter about 30 to 50 mm, color most near Brown N 200B to Grey 201A; first major branch diameter 20 to 30 mm, color most near Grey 201B, two year old cane diameter about 15 to 20 mm, color Greyed Orange 174A; current season wood diameter about 5 to 10 mm, color Yellow Green 145A to 145B.
- *Fruiting wood*.—Numerous twigs of about 15 to 25 cm in length, with internode lengths of about 15 to 20 mm common.

Foliage:

- *Leaf color healthy mature leaves*.—Top side of leaf color is Green 137D, under side of leaf color is Green 138C.
- *Leaf arrangement*.—Alternate, simple.
- *Leaf shape*.—Elliptic.
- *Leaf margins*.—Nearly entire, slight undulations.
- *Leaf venation*.—Pinnate, slightly reticulated.
- *Leaf apices*.—Broadly acuminate.
- *Leaf bases*.—Acute.
- *Leaf dimensions*.—Length: about 55 to 75 mm; width: about 35 to 44 mm.
- *Petioles*.—Small, about 3.0 to 4.0 mm long, about 2.0 to 3.0 mm wide; Color: Yellow Green 145C.
- *Texture*.—Leaf margins, smooth; both upper and lower leaf surfaces, glaucous.

Flowers:

- *Date of* 50% *anthesis*.—5-year average March 15 in south Georgia; March 23 in middle Georgia.
- *Flower shape*.—Urceolate.
- *Flower bud number*.—High, averaging 5 to 8 buds per fruiting shoot.
- *Flowers per cluster*.—6 to 7 common.
- *Flower fragrance*.—Slight rose fragrance often present.
- *Corolla color*.—Red Purple N63C prior to opening, transitioning to White N155B at opening, and finishing at White NN155D.
- *Corolla length*.—About 6.0 to 8.0 mm.
- *Corolla width*.—About 6.0 to 7.0 mm.
- *Corolla aperture width*.—About 3.0 to 3.5 mm.
- *Flower peduncle*.—Length about 9.0 to 11.0 mm; Color: Yellow Green 145C to 145D, with streaks of Red Purple 63B often present.
- *Flower pedicel*.—Length about 3.0 to 4.0 mm; Color: Green 139D.
- *Calyx* (*with sepals*).—Diameter: about 8.5 to 9.5 mm; Color: Green 138C; sepals Green 139D.
- *Stamen*.—Length: about 5.5 to 6.0 mm; number per flower: about 10; filament color: Yellow Green 145D.
- *Style*.—Length: about 7.5 to 8.5 mm; Color: Green 139D.
- *Pistil*.—Length: about 9.0 to 10.0 mm; ovary color: Green 138C.

*Anther*.—Length: about 2.5 to 3.0 mm; number: 10; Color: Greyed Orange 164A.

*Pollen*.—Abundance: high; Color: Yellow White 158A to 159B.

*Compatibility*.—The cultivar has a small to moderate degree of self-compatibility.

Fruit:

*Date of* 50% *maturity*.—5-year average May 8 in south Georgia and May 25 in middle Georgia.

*Fruit development period*.—*About* 52 to 60 days.

*Berry color*.—With wax Blue 100D; with wax removed Black 202A.

*Berry flesh color*.—Green White 157B.

*Berry surface wax abundance*.—High to very high.

*Berry weight*.—$1^{st}$ harvest: about 2.6 to 3.0 g; $2^{nd}$ harvest: about 2.0 to 2.7 g.

*Berry size*.—Height from calyx to scar: about 15 to 18 mm; diameter: about 17 to 20 mm.

*Berry shape*.—Semi-spherical.

*Fruit stem scar*.—Small to medium, dry, no tearing.

*Calyx*.—Depth about 2.0 to 3.0 mm; width, about 5.0 to 6.0 mm; sepals semi-erect to erect when present.

*Berry firmness*.—Medium firm.

*Berry flavor and texture*.—Mildly sweet, very smooth texture, low to medium acidity.

*Storage quality*.—Good.

*Suitability for mechanical harvesting*.—Not suitable.

*Uses*.—Intended for home gardens, but also likely suitable for commercial production in some areas.

Seed:

*Seed abundance in fruit*.—Medium, about 15 or more fully developed seeds/berry.

*Seed color*.—Greyed Orange 164B to 165C.

*Seed dry weight*.—About 40.3 mg per 100 seed.

*Seed size*.—About 1.0 to 1.5 mm long; about 0.5 to 0.8 mm wide.

It is claimed:

1. A new and distinct cultivar of the *Vaccinium* plant named 'TH-920' as illustrated and described herein.

* * * * *